US006849237B2

(12) United States Patent
Housefield et al.

(10) Patent No.: US 6,849,237 B2
(45) Date of Patent: Feb. 1, 2005

(54) BODY FLUID TEST APPARATUS WITH DETACHABLY MOUNTED PORTABLE TESTER

(75) Inventors: T. Scott Housefield, Coconut Grove, FL (US); Matthew Scott Wallace, New Palestine, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 351 days.

(21) Appl. No.: 10/131,437

(22) Filed: Apr. 24, 2002

(65) Prior Publication Data

US 2002/0170823 A1 Nov. 21, 2002

Related U.S. Application Data

(60) Provisional application No. 60/291,890, filed on May 18, 2001.

(51) Int. Cl.[7] .................. G01N 27/327; G01N 21/00

(52) U.S. Cl. .............. 422/82.01; 422/58; 204/403.03

(58) Field of Search ............... 204/403.02, 403.03; 600/300, 316, 344–348; 422/82.01–82.03, 82.05, 55, 58; 205/775, 777.5, 778, 789, 792

(56) References Cited

U.S. PATENT DOCUMENTS

| 5,266,179 | A | 11/1993 | Nankai et al. |
| 5,366,609 | A | 11/1994 | White et al. |
| 5,507,288 | A | 4/1996 | Blasberg et al. |
| 5,597,532 | A | 1/1997 | Connolly |
| 5,854,074 | A | * 12/1998 | Charlton et al. .............. 436/46 |

FOREIGN PATENT DOCUMENTS

| WO | WO 00/05581 | 2/2000 |
| WO | WO 00/07013 | 2/2000 |
| WO | WO 00/47109 | 8/2000 |

* cited by examiner

Primary Examiner—Alex Noguerola
(74) Attorney, Agent, or Firm—Maginot, Moore & Beck (57) ABSTRACT

A test apparatus having a base which performs a plurality of tests for different analytes in body fluids. A portable tester, such as a glucose meter, is detachably mounted to the base and provides a convenient and ergonomic hand-held instrument which a diabetic may carry to frequently monitor blood glucose levels. When mounted or docked to the base, the portable tester is data linked to the base. The invention provides a communications network among the base, the portable tester and another device such as a PC. The portable tester can therefore be kept small and inexpensive since advanced computing and data storage capabilities are provided in the base or a PC.

19 Claims, 6 Drawing Sheets

BODY FLUID TEST APPARATUS WITH DETACHABLY MOUNTED PORTABLE TESTER

RELATED APPLICATIONS

This application claims priority to U.S. Provisional Patent Application Ser. No. 60/291,890, filed May 18, 2001.

FIELD OF THE INVENTION

The present invention relates generally to devices used for the testing of body fluids such as blood and urine and more specifically to portable patient-operated devices for the testing of body fluids.

BACKGROUND

It is estimated that 16 million Americans have diabetes. Those people who have "type 1 diabetes," also called insulin-dependent diabetes mellitus (IDDM), do not produce insulin and need regular shots of it to maintain their blood glucose at a normal level. As a result, people with type 1 diabetes must test their blood sugar regularly, often several times a day, to determine the amount of insulin to be injected. Devices for testing glucose levels in blood are known in the art, a representative example of which being disclosed in U.S. Pat. No. 5,597,532, which is hereby incorporated by reference in its entirety. Many other electrochemical and colorimetric test devices are known in the art.

People suffering from diabetes are often at a higher risk for other diseases. For example, cardiovascular disease is by far the leading cause of death in the United States, and people with diabetes are at much higher risk. Diabetes also contributes to kidney disease, or "nephropathy," which occurs when the kidneys do not filter properly and protein leaks into urine in excessive amounts, which eventually can cause kidney failure. Diabetes is a leading cause of damage to the retina at the back of the eye and also increases risk of cataracts and glaucoma. Nerve damage caused by diabetes, especially in the legs and feet, may interfere with the ability to sense pain and contributes to serious infections.

Because of their higher risk of other complications caused by diabetes, people having the disease must periodically monitor blood or urine for substances other than glucose to ensure good health. For example, the concentrations of total cholesterol, HDL cholesterol and triglycerides provide an indicator of the risk for cardiovascular disease, and can be measured by sampling blood. Test strips and methods for using same are well-known in the art. Similarly, ketone monitoring is also important to detect diabetic ketoacidosis, which results from consistently high glucose levels and stressful events. Unlike glucose monitoring, however, testing for these other "analytes" need be conducted less frequently, perhaps once or twice per month.

What is needed is a testing apparatus that addresses a diabetic's need to monitor blood glucose levels frequently and to monitor other body fluids on a less frequent basis.

SUMMARY OF THE INVENTION

The present invention provides a test apparatus having a base which performs a plurality of tests for different analytes in body fluids. A portable, hand-held glucose meter is detachably mounted to the base and provides a convenient instrument which a diabetic may carry to frequently monitor blood glucose levels. When mounted or docked to the base station, the portable glucose meter is data linked to the base.

In one form thereof, the present invention provides an apparatus for testing body fluids. The apparatus includes a base having a slot adapted for receipt of a test strip and a first display that displays concentration of an analyte in the sample contained in the test strip. A portable tester is detachably mounted to the base, and includes a port that receives a test strip and a second display. The portable tester is operable when detached from the base.

In a preferred form, the portable tester is data linked to the base when mounted thereto. Although the portable tester could be configured to measure and display any of a variety of analytes, portable testers embodying the present invention will typically measure and display glucose concentration. Preferably, the base can measure and display several analytes by means of calorimetric and/or electrochemical tests.

In another preferred form, the base includes a communication connection such that data stored in the base can be downloaded to a computer. Further, the data link between the portable tester and the base allows data stored in the portable tester to be downloaded to the base and in turn to the computer.

One advantage of the present invention is that it addresses the diabetic's frequent need to monitor blood glucose and less frequent need to monitor the levels of other substances, such as cholesterol and ketones. With the apparatus of the present invention, the diabetic can carry the hand-held, portable tester with her at all times and monitor glucose levels several times per day as needed. On the other hand, the diabetic may employ the base station to conduct the full panoply of tests on a less frequent basis. The present invention thus provides a convenient approach for the diabetic, allowing her to carry only the test apparatus she is going to use but not sacrificing the ability to perform more extensive tests as needed.

As a related advantage, it is believed that the present invention actually encourages the diabetic to monitor her glucose levels as needed. That is, by enhancing the ergonomics, simplicity and portability of the hand-held glucose tester, the diabetic is most inclined to use it.

Another advantage of the present invention is that it allows the diabetic to initially purchase only the portable glucose tester, which can be marketed and operated as a "stand-alone" device. The diabetic can later "upgrade" by purchasing a compatible base unit.

Yet another advantage of the present invention is that it provides modular capabilities. For example, a portable glucose tester that becomes lost or malfunctions can be cost-effectively replaced without replacing the entire unit. Some diabetics may even prefer to own two or more portable testers, e.g., one for the office and the other for use at home, both of which would be compatible with a single base. By the same token, some patients may desire more than one base unit compatible with a single portable glucose tester, for example, a patient having two residences. This modular capability also allows design and marketing of two or more different base models that are compatible with the same glucose tester. For example, one base unit may provide four tests, whereas a "deluxe" model may offer six or more tests. Such a modular approach provides more choices to the patient and her physician. All of these and other modular capabilities are made possible by the present invention._

Still another advantage of the present invention is that communications and functional capabilities of the hand-held glucose meter are not compromised by its portability. By means of the data link provided between the hand-held glucose meter and the base when the two are "docked," data collected by the hand-held meter can be downloaded to the base unit. In turn, data stored in the base unit can be downloaded to a computer, which may then be transmitted electronically to the patient's physician. Further, by incorporating more extensive testing, computing and memory storage capabilities in the base unit or a PC, a smaller, more ergonomic and more cost effective design of the portable tester is possible.

BRIEF DESCRIPTION OF DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
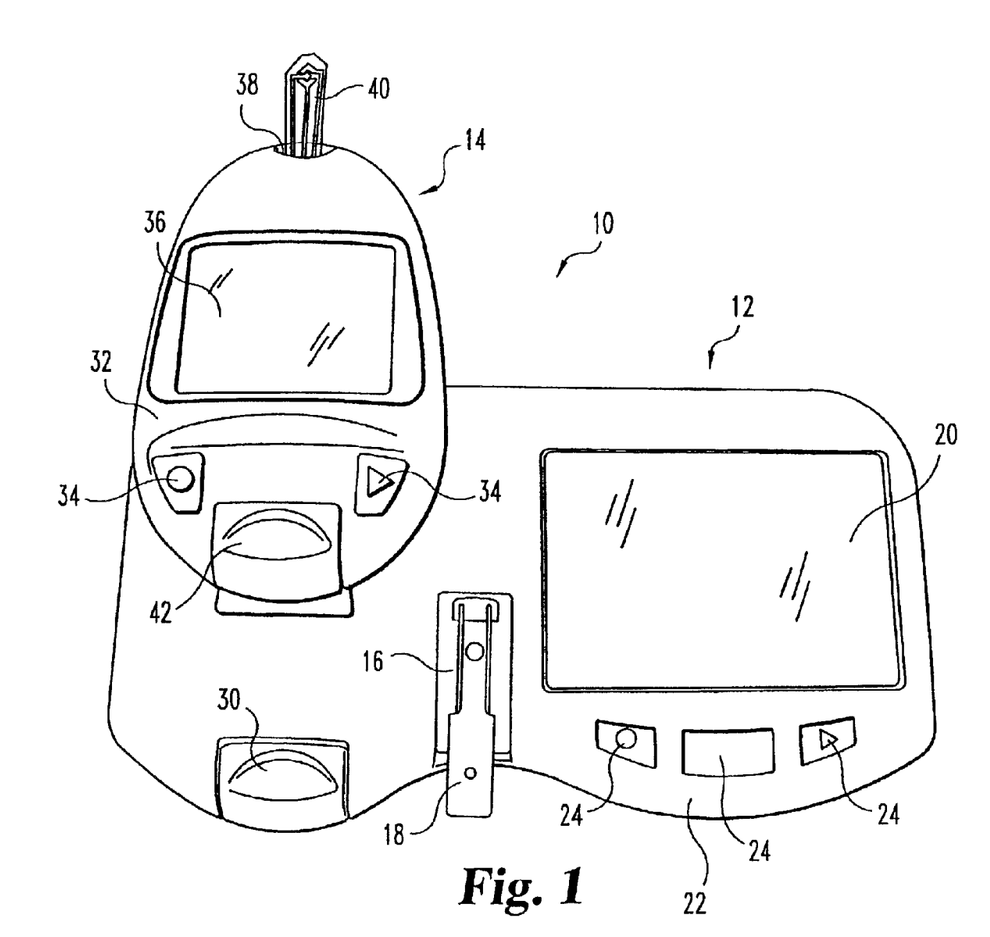
FIG. 1 is a perspective view of an apparatus for testing body fluids illustrating the multi-test base unit having the portable glucose tester detachably mounted thereto.
Figure 2:
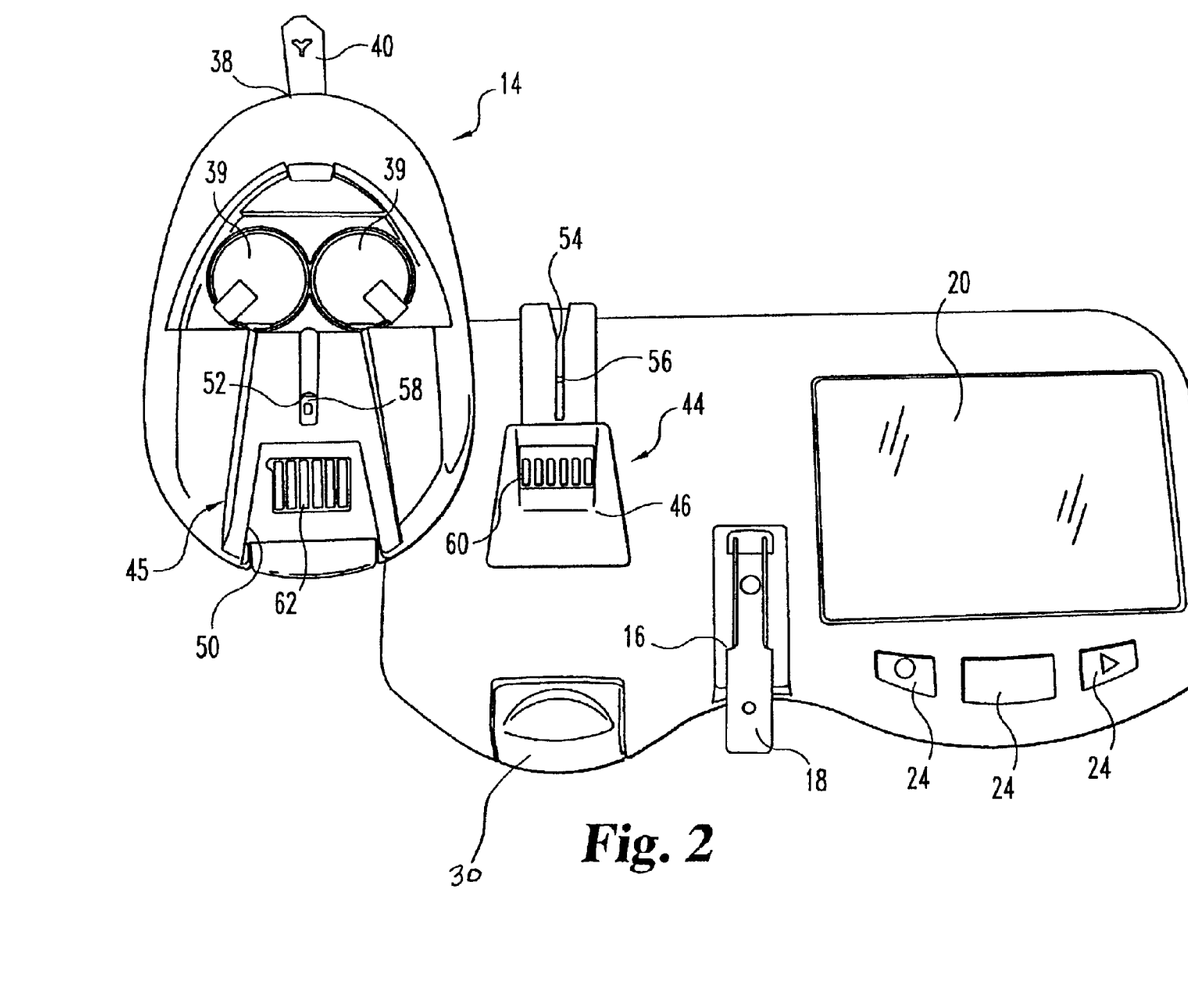
FIG. 2 is a perspective view of the apparatus shown in FIG. 1, illustrating the portable tester detached from the base and flipped over.
Figure 3:
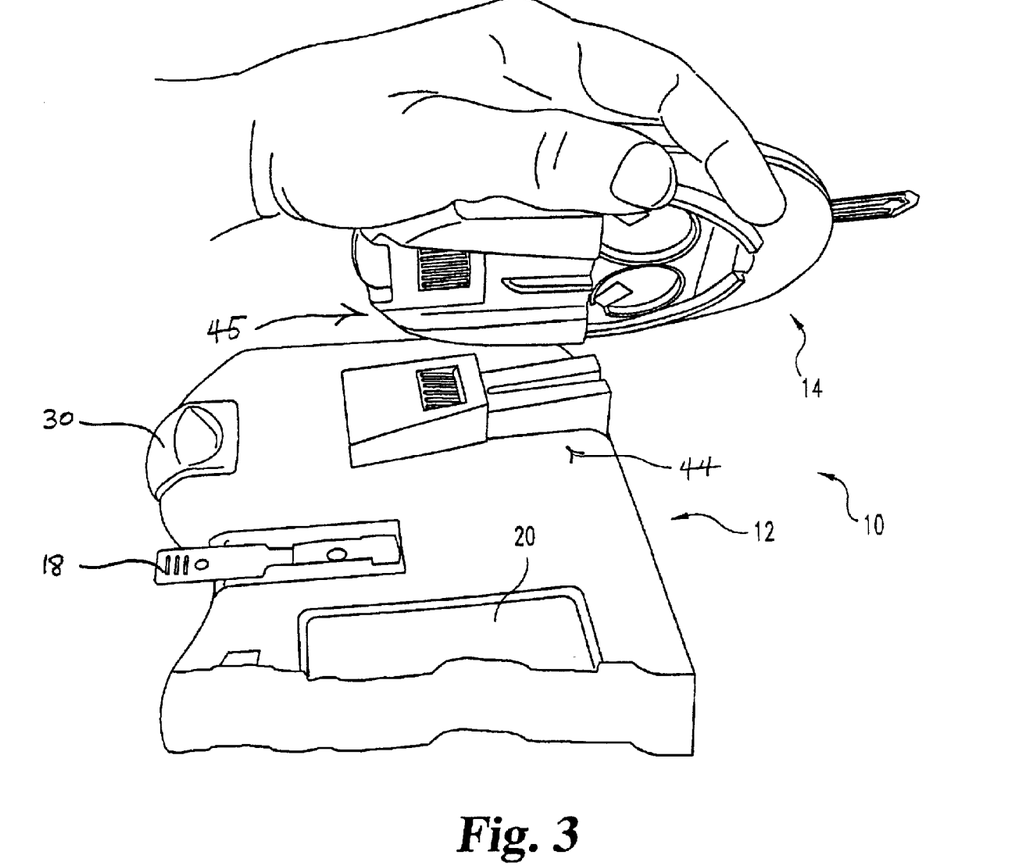
FIG. 3 is a perspective view of the apparatus shown in FIG. 1, illustrating the docking station provided on the base, the coupling on the portable tester and the mating relationship therebetween.

Referring now to FIGS. 1–3, apparatus 10 includes base or base station 12 and portable glucose meter 14 detachably mounted thereto. Base 12 can be configured to perform a battery of tests such as glucose, total cholesterol, triglycerides, and blood urea to name just a few. One device essentially suitable for base 12, the modifications thereto being noted below, is the apparatus disclosed in U.S. Pat. No. 5,597,532, which is hereby incorporated by reference in its entirety. A commercially available device manufactured in accordance with the '532 patent is available from Polymer Technology Systems, Inc., Indianapolis, Ind., under the trademark BioScanner 2000™.

Figure 6:
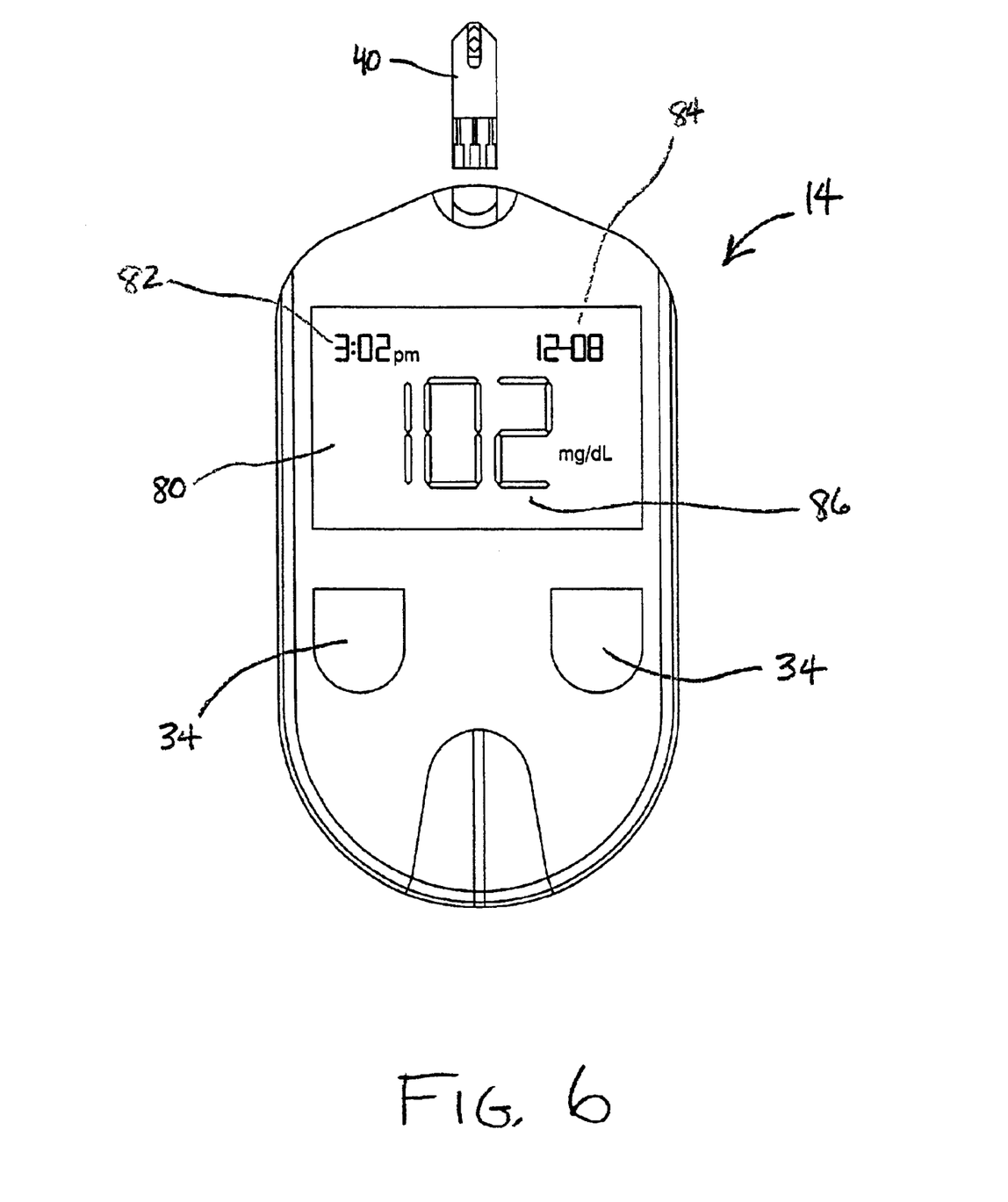
FIG. 6 is a plan view of a display suitable for both the portable tester and base unit in accordance with the present invention.

Base 12 includes slot 16 which receives and retains test strip 18 as shown. Test strips such as the general type disclosed in the '532 patent can be used with base 12, for example. A liquid crystal display 20 displays the concentration of an analyte in the sample contained in test strip 18. An LCD display suitable for use with the base station (or portable tester 14) is shown in FIG. 6. Display 80 indicates time 82, date 84, and concentration of analyte in mg/dL 86. Other parameters can be displayed. For example (FIG. 1), by operating interface keypad 22 having operator keys 24, the user may display other data, such as history of results for a specific test.

Figure 4:
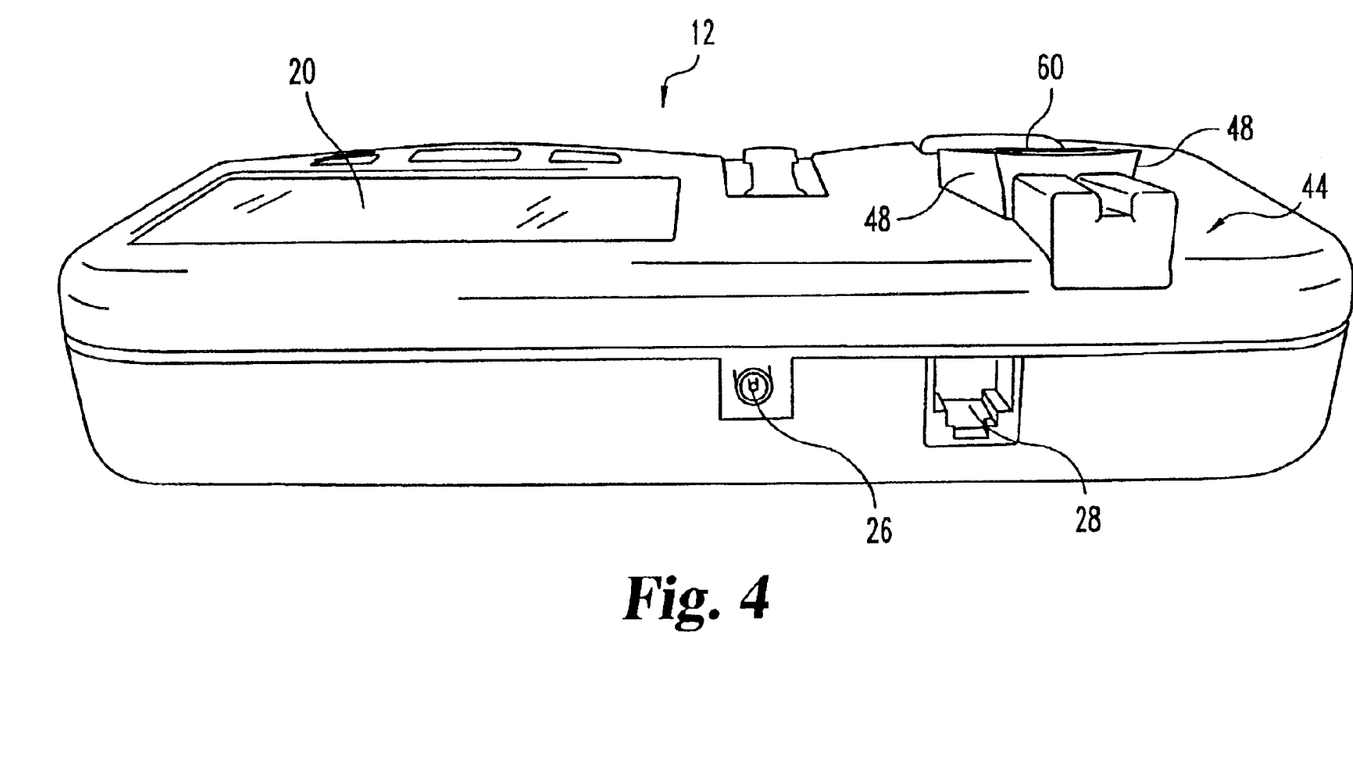
FIG. 4 is a perspective view of the apparatus shown in FIG. 1, taken from the rear of the unit and illustrating the PC connector and the external power connector.

With reference to FIG. 4, base 12 includes external power connector 26, which is adapted for a 12 volt DC adapter (not shown). A battery supply (not shown), such as three AA batteries, for example, may also be provided for base 12. Base 12 also includes PC connector 28 which, in the present embodiment, is configured as a standard RS-232 connector. Depending upon the specific tests performed by base 12 and communications capabilities desired, software to support the connection can be readily written by one of ordinary skill in the art. A removable EEPROM or "Memory chip" 30 is provided as shown and works similar to that described in U.S. Pat. No. 5,597,532. The reader is referred to the '532 patent and the attached appendix for a more detailed discussion of the Memory chip.

Portable tester 14 in the illustrated embodiment measures the level of an analyte in a body fluid. Portable testers embodying the present invention will typically test glucose levels in blood samples, although it is envisioned that portable tester 14 could be configured to test other fluid samples, or be configured to conduct a plurality of tests. It is envisioned that portable testers 14 embodying the present invention will preferably conduct electrochemical tests, as opposed to colorimetric tests, because electrochemical tests are less light sensitive and the portable tester is likely to be used under conditions of widely varying lighting. Electrochemical glucose tests are well-known in the art and examples of same can be found in U.S. Pat. Nos. 5,366,609 and 5,266,179. Alternatively, portable tester 14 may be configured to perform calorimetric tests.

Portable tester 14 includes case 32, the inside of which contains the circuitry and microprocessor for portable tester 14. With reference to FIG. 1, portable tester 14 includes user input keys 34 and LCD display 36, which may be the same or similar to display 20 of base 12. A representative sample of an LCD suitable for display 36 is illustrated in FIG. 6. Port 38 is configured to receive a glucose test strip 40 as shown. Portable tester 14 also includes a Memory chip 42 which functions in the same manner as Memory chip 30, described above. Portable tester 14 includes its own power supply such that it is operable independently of base 12. As shown in FIG. 2, portable tester 14 includes round recesses 39 that house lithium batteries (not shown). In use, a removable cover (not shown) covers recesses 39 that house the batteries.

Turning now to FIGS. 2 and 3, an embodiment of the docking mechanism of the present invention can be appreciated. The primary difference between base 12 and the tester shown and described in the '532 patent (or any body fluid tester for that matter) is that base 12 includes docking station 44 which mates with coupling 45 on the underside of portable tester 14. It can also be appreciated that portable tester 14 differs from known testers by the inclusion of coupling 45. Docking station 44 includes a tapered hub 46 having outwardly flared sidewalls 48 (See FIG. 4). Hub 46 slides into corresponding tapered recess 50 formed in the bottom side of tester 14. Coupling 45 includes an elongate protuberance 52 that slides into channel 54 of docking station 44. A cross bar 56 formed in channel 54 fits into groove 58 formed in protuberance 52. When sliding or "docking" portable tester 14 into base 12, the engagement of cross bar 56 and groove 58 provides the user with a tactile sensation that the portable tester is properly mounted to base 12. Portable tester 14 is removed from base 12 by sliding it upwardly and toward the rear of the base.

With further reference to FIGS. 2 and 3, docking station 44 includes male connector 60 which mates and communicates with female connector 62 of coupling 45. Connectors 60 and 62 are "Bourns" connectors commercially available from Rathsburg Association in Novi, Mich., sold under part numbers 70AAJ-4-MIG and 70AAJ-4-FIG, respectively. Connectors 60 and 62 form a data link between tester 14 and base 12 when docked. That is, when docked, the microprocessors of portable tester 14 and base 12 can exchange data in accordance with data communication methods known to one of ordinary skill in the art. (See FIG. 5). Connectors 60 and 62, or similar connectors could be used to conduct electricity to the portable glucose tester to, for example, recharge a rechargeable battery (not shown) housed in portable tester 14.

It is envisioned that the data exchange between portable tester 14 and base 12 will include data stored in portable tester 14 being downloaded to base 12 at regular intervals and the memory in portable tester 14 then being erased so that memory space is made available for storage of new data in portable tester 14. Further, it is envisioned that portable tester 14 could be reprogrammed by base 12 when docked thereto. Many other uses for the data link between base 12 and portable tester 14 would be readily recognized by one of ordinary skill in the art and such uses are contemplated by this disclosure.

Figure 5:
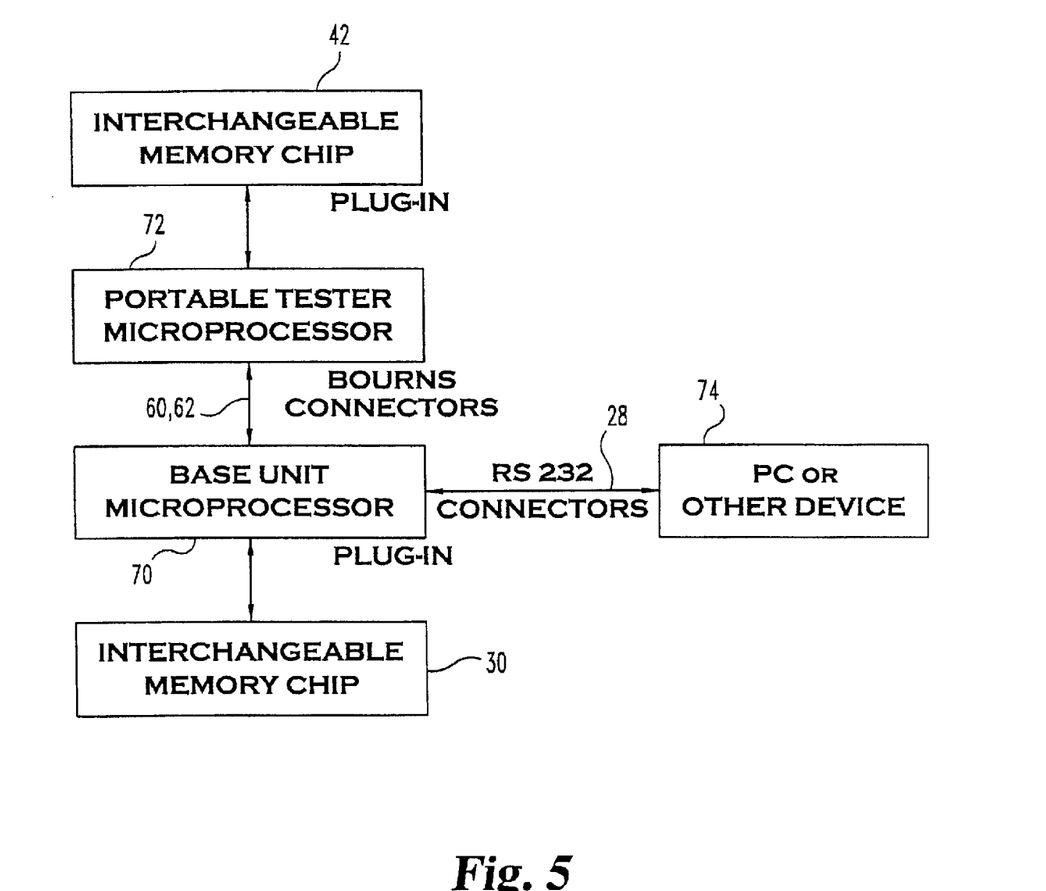
FIG. 5 is a block diagram representing the communications network formed among the microprocessors of the base and portable testers, their interchangeable Memory chips, and the external PC connection.

Turning now to FIG. 5, microprocessor 70 of base 12 includes digital integrated circuitry and is used to time selected tests, read signals, and together with associated programs and data memory, calculates and stores values of analytes tested in base 12. Additional information may be stored in interchangeable Memory chip 30 as discussed above and in more detail in the '532 patent incorporated herein by reference. Microprocessor 70 is programmed to receive, analyze and store data from microprocessor 72 of portable tester 14 and communicates with same through Bourns connectors 60, 62 discussed above. Microprocessor 70 communicates via RS 232 connectors to PC 74 or similar device.

Microprocessor 72 of portable tester 14 and interchangeable Memory chip 42 operate in much the same manner as do microprocessor 70 and chip 30, respectively. However, for most applications, it is envisioned that microprocessor 72 need not have as extensive a computing and memory capacity as does microprocessor 70, since portable tester 14 will typically only conduct a single test, viz., glucose level, and store data for a period of only 14–30 days before downloading to processor 70. Through the communications network shown, both microprocessors 70 and 72 can be programmed by or through PC 74. Further, microprocessor 72 can be reprogrammed by microprocessor 70.

Because of the communications link among the components of the disclosed apparatus, modular capabilities are achieved. For example, a portable tester that is lost or malfunctions can be economically replaced without replacing the base unit. Further, the communications capabilities disclosed herein allow a smaller, more ergonomic and more cost-effective design of portable tester 14 because much of the advanced system capabilities are contained within the more comprehensive base unit 12 and/or PC 74 to which portable tester 14 can be linked.

While a preferred embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A diagnostic apparatus for testing body fluids, comprising:
    a base having:
        a slot adapted for receipt of a first test strip;
        a first display configured to display the concentration of an analyte in a body fluid sample contained in the first test strip; and
        a docking station adapted to detachably receive a portable tester; and
    a portable tester detachably mountable to said base, said portable tester having a second display and a port adapted to receive a second test strip containing a body fluid sample, said portable tester operable to test the sample contained in said second test strip when detached from said base.

2. The apparatus of claim 1, wherein said portable tester is data linked to said base when mounted thereto.

3. The apparatus of claim 1, wherein said portable tester is configured to measure and display glucose concentration.

4. The apparatus of claim 1, wherein said portable tester is configured for electrochemical testing.

5. The apparatus of claim 4, wherein said portable tester is configured to measure glucose concentration.

6. The apparatus of claim 1, wherein said base is configured to measure and display the concentration of at least two analytes.

7. The apparatus of claim 1, wherein said base is configured for calorimetric testing.

8. The apparatus of claim 1, wherein said base further comprises an external communication connection.

9. A portable tester for measuring the concentration of an analyte in a body fluid, said portable tester comprising:
    a portable hand-held tester body having a port adapted for receipt of a test strip containing a body fluid sample and configured to determine the concentration of the analyte in the sample;
    a display for displaying the concentration of the analyte; and
    a coupling adapted for detachably mounting said tester to another device.

10. The portable tester of claim 9, further comprising a data connector adapted for transmitting data stored by said portable tester.

11. The portable tester of claim 9, wherein said portable tester comprises an instrument to measure concentration of glucose in a body fluid.

12. The portable tester of claim 9, further comprising a base unit to which said portable tester is detachably mountable, said base unit being configured to measure and display the concentration of at least two analytes.

13. The portable tester of claim 12, wherein said base includes at least one colorimetric test.

14. The portable tester of claim 13, wherein said portable tester measures concentration of glucose.

15. A method of monitoring daily glucose levels in a body fluid and periodic levels of at least one analyte other than glucose, said method comprising:

(a) using a hand held portable tester to measure the daily glucose levels; and (b) periodically docking the portable tester to a base, the base being configured to measure the at least one analyte other than glucose.

16. The method of claim 15, further comprising downloading data or information from the hand held portable tester to the base.

17. The method of claim 16, further comprising operably connecting the base to a computer.

18. The method of claim 15, further comprising using the base to test a body fluid for the at least one analyte other than glucose.

19. The method of claim 18, further comprising using the base to test at least two analytes other than glucose.

* * * * *